United States Patent [19]
Rubins

[11] Patent Number: 6,071,229
[45] Date of Patent: Jun. 6, 2000

[54] VIDEO OR COMPACT DISK ENCODER/ DECODER FOR BRAIN WAVE SYNCHRONIZER

[76] Inventor: Tye Rubins, 2073 Sunset Plaza Dr., Los Angeles, Calif. 90069

[21] Appl. No.: 08/216,684

[22] Filed: Mar. 23, 1994

Related U.S. Application Data

[63] Continuation-in-part of application No. 08/164,001, Dec. 8, 1993, Pat. No. 5,409,445, which is a continuation-in-part of application No. 07/878,825, May 5, 1992, Pat. No. 5,306,228.

[51] Int. Cl.$^7$ ................................................. A61M 21/00
[52] U.S. Cl. ............................................................ 600/27
[58] Field of Search .......................................... 600/26–28

[56] References Cited

U.S. PATENT DOCUMENTS

| | | |
|---|---|---|
| 4,902,274 | 2/1990 | Gleeson, III . |
| 5,036,858 | 8/1991 | Carter et al. . |
| 5,149,317 | 9/1992 | Robinson . |
| 5,306,228 | 4/1994 | Rubins . |

*Primary Examiner*—John P. Lacyk
*Attorney, Agent, or Firm*—Oppenheimer Wolff & Donnelly LLP

[57] ABSTRACT

A video decoder driving a sensory stimulation transducer by decoding, transforming or converting encoded data in a video signal to an output from a sensory stimulation transducer. In another aspect, a digital decoder driving a sensory stimulation transducer by decoding, transforming or converting encoded data in a subcode, or allocated, region of a storage medium to an output from a sensory stimulation transducer. The sensory stimulation transducer may be a brain wave synchronization device, such as light producing devices delivering light to a user's retina. In another aspect, a method and apparatus for pulsing light delivered by the light producing device thereby enhancing the entrainment associated with brain wave synchronization in the user.

43 Claims, 6 Drawing Sheets

VIDEO OR COMPACT DISK ENCODER/DECODER FOR BRAIN WAVE SYNCHRONIZER

This is a continuation-in-part of application Ser. No. 08/164,001, filed Dec. 8, 1993, now U.S. Pat. No. 5,409,445, which is in turn a continuation-in-part of application Ser. No. 07/878,825 filed May 5, 1992 now U.S. Pat. No. 5,306,228.

BACKGROUND OF THE INVENTION

1. Field of the Invention

The present invention relates to an apparatus for decoding encoded sensory stimulation data embedded in a video signal or digital storage medium for presentation to a user, and more particularly, to influencing brain waves and learning activity in a user by presenting periodic visual and audio signals to the eyes and ears of the user or by presenting other sensory inputs to the user alone or in conjunction with conventional information.

2. Description of Related Art

It is well known that the human brain generates periodic electrical signals, commonly referred to as "brain waves." These brain waves range in frequency from about 1 Hz to about 36 Hz and, for ease of reference, are commonly divided into four or more groups. "Beta" waves (12 to 36 Hz) tend to dominate in the brain during normal waking activity; "Alpha" waves (8 to 12 Hz) have been discovered to occur most frequently when the person is relaxed; "Theta" waves (4 to 7 Hz) are most common during periods of sleep or deep meditation and also occur during periods of learning or memory recall; and "Delta" waves (1 to 4 Hz) appear most frequently during periods of the deepest sleep. These ranges of frequencies are approximate, but in general, the dominate brain wave frequency increases with increasing mental activity.

Experiments have indicated that when light is repeatedly flashed into the eyes of a subject within this frequency band, the brain waves of the subject tend to assume the frequency of the flashing light. It has also been discovered that such "synchronization" of brain waves may lead to brain seizures in epileptics or in other people who have a history of brain seizures.

On the other hand, experiments have demonstrated that pulsating light and sound can induce a synchronized pattern of brain waves. There is, furthermore, evidence to indicate that by inducing a subject's brain waves to come within the Alpha range, the subject at least will be able to relax better, and may even be able to learn more quickly and permanently. Many researchers also report that a subject whose brain waves are caused to synchronize within the Alpha range or lower are better able to receive subliminal or audible audio messages.

Differential audio frequencies have also been shown to cause similar effects. For example, if the frequency of a tone played into one ear of a subject is 10 Hz higher than the frequency of a tone played into the subject's other ear, experimental evidence indicates that the subject's brain acts in a way similar to a "heterodyne," tending to generate brain waves at a frequency approximately equal to the difference in frequency between the two tones. That is, in this case, 10 Hz. The same result arises when tones are alternately put to the left and right ears with a frequency equal to the desired synchronization frequency.

There are accordingly many devices now available that are designed to present flashing lights, alternating tones, or both, to the eyes and ears of a user. Some devices use "bio-feedback," in which the brain wave frequency of the user is sensed and used to control the frequency of the flashing lights or pulsating tones; the user thereby attempts to train herself to produce the desired frequency, which is reinforced by the flashing lights and pulsating tones. Many other devices, which do not measure the brain waves in an attempt to create a feedback loop, actively control the flashing or switching frequency. Examples of such devices are described in the following U.S. Patents:

| No. | Inventor(s) | Issue Date |
| --- | --- | --- |
| 5,064,410 | Frenkel, et al. | Nov. 12, 1991 |
| 5,036,858 | Carter, et al. | Aug. 6, 1991 |
| 4,955,389 | Schneider | Sept. 11, 1990 |
| 4,902,274 | Gleeson, III | Feb. 20, 1990 |
| 4,834,701 | Masaki | May 30, 1989 |
| 4,665,926 | Leuner, et al. | May 19, 1987 |
| 4,632,126 | Aguilar | Dec. 30, 1986 |
| 4,456,347 | Stahly | June 26, 1984 |
| 4,396,259 | Miller | Aug. 2, 1983 |
| 4,335,710 | Williamson | June 22, 1982 |
| 4,315,502 | Gorges | Feb. 16, 1982 |
| 4,008,714 | Silva, et al. | Feb. 22, 1977 |
| 3,882,850 | Ballin, et al. | June 13, 1975 |

All of these known devices create the synchronizing pulsed light and/or sound by actively generating an electrical pulse at the desired frequency. This electrical synchronization pulse activates a small set of lights in front of the user's eyes, and controls a tone generator whose signal is fed into earphones. In many of these conventional devices, the electrical pulses result from a timing program in the memory of a microprocessor or a computer. In some of these devices, the user herself selects the synchronization frequency. In other devices, one or more frequencies or programs of varying frequency are generated automatically, whereby the user, in some cases, can select which program she wishes to follow.

The foremost drawbacks of known devices for synchronizing brain waves are that they are complicated and expensive. They typically contain many mechanical and electrical components that require careful testing and calibration. Few are suitable for easy use by most individuals, and fewer still are within their budgets. Even the least expensive of these known devices sells at retail for prices on the order of hundreds of dollars. Additionally, there appear to be no known devices capable of using an encoded video signal or an encoded compact disk subcode signal to economically stimulate a user's senses, for example, by inducing synchronized brain waves by providing data for driving flashing lights, producing pulsating tones, and/or controlling the release of odors.

In order to reduce complexity, at least one device (see the patent to Gleeson) encodes control signals on magnetic tape. Such devices, however, typically require four or more audio channels simultaneously, so that they are not suitable for use in common 2-channel devices such as the portable stereo cassette tape players already owned by a large section of the population. Furthermore, the Gleeson device requires special conditioning circuitry separate from the tape player in order to drive the lights and speakers used; this increases design costs.

It is therefore an object of this invention to provide a device for inducing synchronized brain waves using both flashing lights and pulsating tones that is easy to use and that can be manufactured from inexpensive and compact components so as to make it much more affordable than existing devices. It is another object to adapt the present invention to a personal computer. It is yet another object of the present invention to detect when a user enters the Delta brain wave state.

A still further object is to inexpensively decode video signals or compact disk subcode signals to induce synchronized brain waves by responsively driving flashing lights and/or pulsating tones. Additionally, an object is to provide a device for responsively controlling odor producing devices, or other sensory transducers, possibly to be used to facilitate augmented learning ability in a device user. A further object of the present invention is to enhance the degree of entrainment in a user of a brain wave synchronization device by providing a method of delivering pulsed light to the user's retinas having a relatively high actual peak intensity and a relatively short duration.

SUMMARY OF THE INVENTION

In one broad aspect, the present invention provides a video decoder sensory stimulation system for controlling the stimulation of a user's senses based on decoded data from an encoded video signal. A video signal is encoded with sensory stimulation data, such as brain wave synchronization data, using a suitable encoding scheme provided by an exemplary encoder of the present invention. The encoded signal may be stored, transmitted or broadcast as desired. An exemplary video decoder in accord with the present invention recovers the encoded data from an incoming video signal and decodes, converts, or transforms the data into control data for operating a sensory stimulation transducer. The transducer may be a brain wave synchronization transducer or an odor producing device, among others. Accordingly, a sensory stimulation device receiving a video signal including encoded data comprises a detection circuit receiving said video signal and detecting said encoded data and a control circuit operating on said detected encoded data and responsively controlling at least one sensory stimulation transducer.

Another broad aspect of the present invention provides for digital decoding of sensory stimulation data embedded in a subcode region of a compact disk, or similar, medium. The sensory stimulation data may comprise, for example, brain wave synchronization data for driving a brain wave synchronization transducer, such as LEDs. Other types of sensory stimulation transducers may be used, however, such as buzzers, odor producing devices, or the like. Accordingly, a sensory stimulation device comprises a storage medium having a plurality of allocated storage regions, at least one of said allocated regions including encoded sensory stimulation data; a retrieval device for accessing data from said storage medium and serially providing an encoded output; a control circuit including a register receiving said encoded output and storing it as a plurality of bits, a computer, including a digital port, operatively monitoring the value of said plurality of bits in said register and responsively transforming said plurality of stored bits into a plurality of control bits provided to said digital port; and at least one sensory stimulation transducer operatively connected to said digital port.

A further broad aspect of the present invention provides a method of pulsing a light producing device for producing brain wave synchronization to enhance brain wave entrainment in a user of the device. A composite pulsing signal is provided as a combination of synchronization and micro-pulse components such that a higher actual peak intensity of light is delivered to the user's retina for a given level of apparent light intensity observed by the user. Accordingly, a method is provided of producing brain wave synchronization in a user of a light producing device, the device operatively delivering light having an apparent intensity and an actual peak intensity to the user's retina, the method comprising pulsing the light producing device with a composite signal including a synchronization frequency component and a micro-pulse frequency component; wherein said pulsing provides a higher peak intensity for a given apparent intensity, thereby enhancing the brain wave entrainment of the user.

In association with the method above, another broad aspect of the present invention is a pulse driving device producing enhanced brain wave entrainment in a user. Accordingly, a device producing brain wave synchronization in a user comprises a light producing element operatively delivering light to the retina of the user having an apparent intensity and an actual peak intensity; said light being delivered in relatively short pulses at a peak intensity exceeding the apparent intensity observed by the user; wherein brain wave entrainment of the user is enhanced by the use of higher peak intensity light.

DETAILED DESCRIPTION OF THE INVENTION

Figure 1:
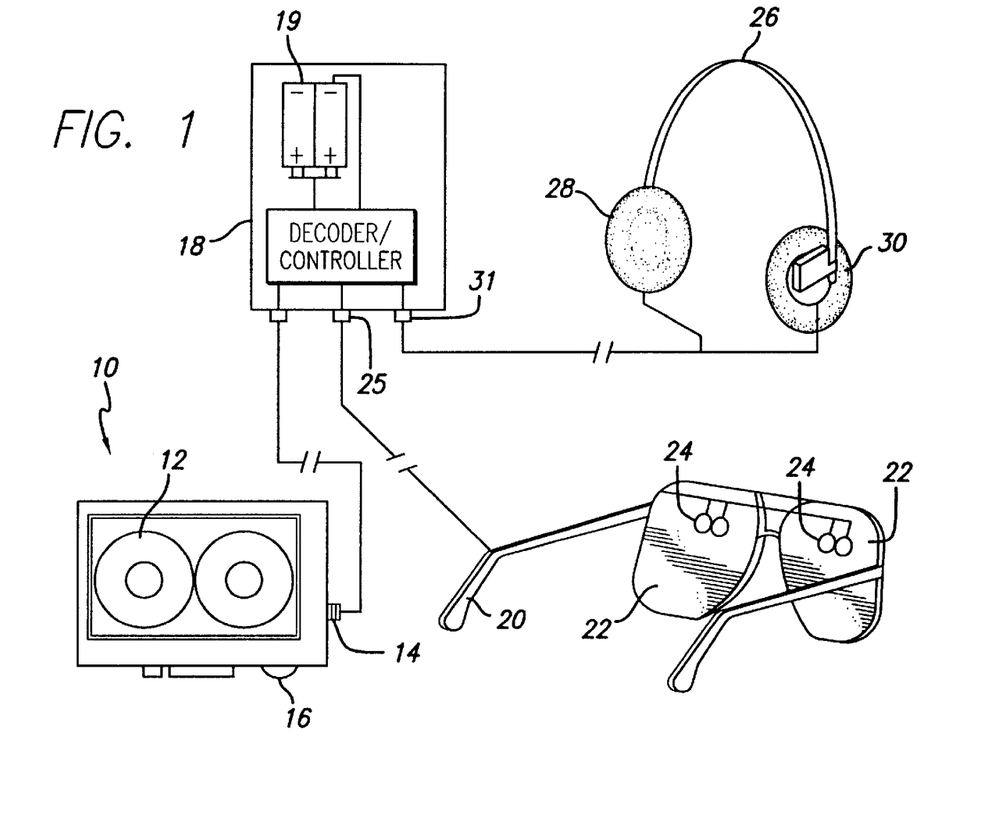
FIG. 1 illustrates the main components and general configuration of the brain wave synchronizer according to the invention.

FIG. 1 shows the main components of the system according to the invention. A standard, commercially available tape player is indicated generally by reference number 10. A standard cassette tape is indicated by reference number 12.

The tape player 10 includes a least one audio output 14 and a volume control 16. It is not necessary according to the invention for the tape player 10 to be portable; instead, any tape player may be used, and application of the invention to other technologies such as reel-to-reel tape players, CD players, and digital audio tape players is also possible. The invention requires only that there be some audio output, for example, the output normally used to connect the tape player to headphones.

According to the invention, the recording medium such as the cassette tape 12 needs one track for recording an audio control signal. If the invention is used in combination with another audio program such as a self-help message or other learning program, the recording medium should have at least one other track for carrying this program. The invention is therefore well-suited for use with a standard stereo cassette tape.

The invention also includes a decoder/controller device 18, whose construction and operation are described below. As FIG. 1 illustrates, the user will normally plug the decoder/controller 18 into the output 14 of the tape player 10. The decoder/controller 18 therefore receives the left and right audio tracks of the stereo output. Either of the left or right track can be used as the control track with the unused track being sent directly to the earphones or speakers. After decoding the control signal (described below), the decoder/controller 18 generates signals that control audio and visual synchronization signals. The decoder/controller 18 also houses one or more standard batteries 19 that provide electric current to the circuity of the decoder/controller.

In order to present flashing visual signals to the eyes of the user, the invention includes glasses 20 with opaque lenses 22 and at least one light 23, 24 mounted on each lens in front of the eye of the user. The glasses 20 are preferably inexpensive, standard glasses whose lenses are covered with an opaque material. This material may be such as a metallic foil, but is it preferably a printed circuit board, which not only shields the user's eye from ambient light, but also carries standard etched or attached conductors that lead electrical current to the lights.

The lights 23, 24 are preferably pairs of light-emitting diodes (LEDs). Such LEDs draw little electrical current and have a sufficiently fast on/off response that the user can clearly sense that they are flashing at or below frequencies in the Beta range. The color of the lights 23, 24 is not essential according to the invention as long as the light is visible. It is not necessary to include two paired lights in front of each of the user's eyes. Paired lights are preferred, however, since they provide a wider field of view than a single LED. This in turn makes the glasses 42 more universally useful and reduces the expense of having to manufacture the glasses with different placement of the lights.

One light per eye may, however, be used if it has sufficiently wide field of view and is sufficiently bright. In this context one should also keep in mind that the user's eyes will usually be closed while she is using the invention, and the flashing of the lights must then be visible through her eyelids.

The glasses 20 are connected to the decoder/controller 18 using a standard electrical connector, jack or plug 25. The number of electrical connectors between the decoder/control and the glasses 20, and why, is explained below.

The invention also includes common stereo earphones with a left speaker 28 and a right speaker 30. The earphones 26 are connected to the decoder/controller using a conventional stereo earphone jack 31.

FIG. 1 illustrates one of the main cost-saving advantages of the invention. Most users will already own a tape player 10 and headphones 26 suitable for use with the invention. Even for those users who do not yet own such equipment, the cost of a satisfactory tape player with accompanying headphones, together with the cost of the decoder/controller 18 and glasses 20 according to the invention, will still be much less than the cost of existing devices designed to synchronize brain waves.

According to the invention, control signals for driving the pulsating lights 23, 24 and alternating audio tones in the earphones 26 are pre-recorded using known recording equipment onto a single tract of the cassette tape or other recording medium. The control signals in the preferred embodiment comprise a superimposition of three separate audio frequencies onto the control track. These frequencies, labelled f1, f2, and f3 below, are sufficiently separated in the audio range that corresponding band-pass filters (described below) are able effectively to filter out the other two frequencies while passing its center frequency, which is approximately the frequency of the corresponding control tone.

Signals f1 and f2 are pulsating sine waves. During the recording process, the rate of pulsation is equal to the desired brain wave frequency ("pulse"). Each pulse's beginning and ending is determined by a preprogrammed or manually operated sequencer, the construction of which is well know within the art. Furthermore, the number of sinusoids within each pulse can be changed, during the recording process, to control the intensity of illumination of the lights, as is explained below. Furthermore, since f3, which is also a sine wave, will be used as the audio tone in the earphones 26, f3 should be chosen to be comfortable to listen to; frequencies within one octave on either side of middle C are, for example, suitable.

Figure 2:
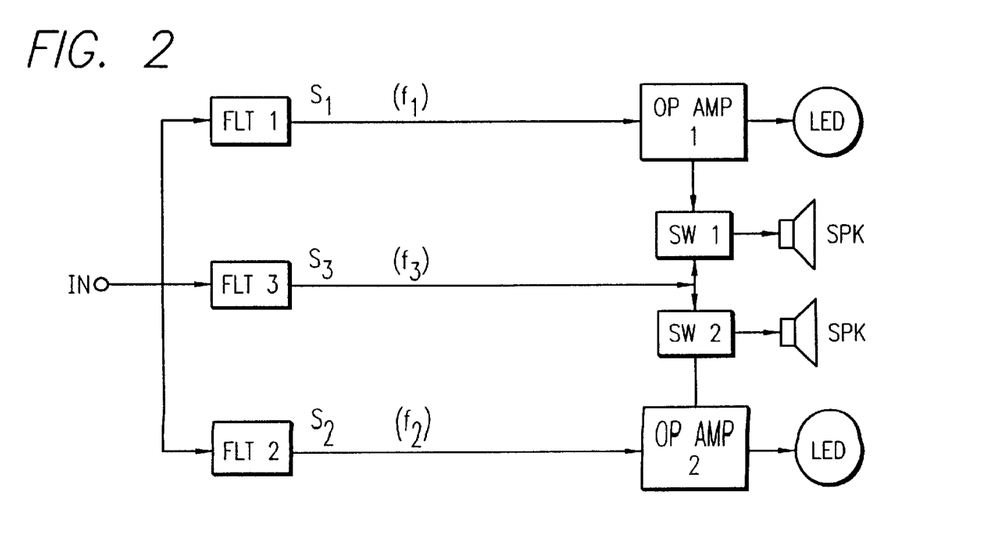
FIG. 2 is a simplified block diagram of the decoding and control circuitry used in the invention.

FIG. 2 is a block diagram that shows the general structure of the circuitry of the decoder/controller 18. The audio input signal from the control track of the cassette tape is indicated at the left as the signal IN. The signal IN first passes to a bank of three filters FLT1, FLT2, and FLT3. The output signals from the filters FLT1, FLT2, and FLT3 are S1, S2, and S3, respectively. The dominant (and for an ideal band-pass filter, the only, frequency of each output signal S1, S2, and S3 , is f1, f2, and f3, respectively. In the preferred embodiment, the filters are band-pass filters, although a low-pass only filter may be used to extract the lowest-frequency control signal from the input signal IN.

Output signals S1 and S2 are both sine waves and are both used in three ways. First, signals S1 and S2 are used to switch on and off LED1 and LED2, respectively. Each signal, S1 or S2, goes to a separate and identical Op Amp. The Op Amp activates a light. Since the frequency of both S1 and S2 is greater than the frequency of the desired brain waves pulse, i.e. greater than 40 Hz and the approximate threshold of human visual perception, the light appears to be on continuously during each pulse.

Second, signals S1 and S2 are used to control the intensity of illumination of the lights. Since the lights are activated, turned on and off, at the same rate as the frequency of the sine waves of S1 and S2, removal of any of the sinusoids from either signal during the recording process will reduce the number of sinusoids going to the respective Op Amp and activating the lights. While the pulse remains unchanged, the reduction in intensity of illumination of the lights during the pulse is directly proportional to the number of sinusoids removed from the signal during the pulse. In other words, this reduces the number of times the lights are activated during the pulse which means the total illumination over the period is reduced.

Figure 4:
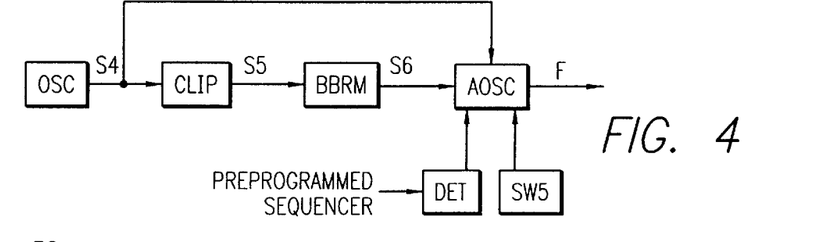
FIG. 4 is a simplified block diagram of the intensity encoding device used in the invention.

One method to accomplish this part of the invention occurs during the recording of F1 and F2 and is illustrated in FIG. 4. Preferably, an oscillator (OSC) generates a continuous sine-wave tone of 2800 Hz (S4); this is an example only and the tone need not be of this frequency. Signal S4 goes through a clipper (CLIP) which shapes the S4 into square waves (S5). Signal S5 is used as a clock for a binary bit-rate multiplier (BBRM). The preprogrammed sequencer activates a detector (DET) which determines the beginning and ending of each pulse. This information goes to the BBRM which pulses signal S6 on and off at the desired brain wave frequency or pulse. A binary switch (SW5) controls the BBRM and determines the number of square waves that will be in each pulse of S6. The signal S6 goes to an analogous sine wave oscillator (AOSC) which produces the signal to be recorded, F (f1 or/and f2). To produce both f1 and f2 with dissimilar or alternating pulsation rates, two such devices as described above would be required. The construction of the above is well-know within the art.

Third, signals S1 and S2 are also used according to the invention to control the switching from one ear to the other of an audio tone into the earphones, (SPK1 and SPK2). This audio tone itself is carried by the third signal S3 and is present at switches SW1 and SW2. The presence of S1 and S2 activates switches SW1 and SW2, respectively. The activation of either SW1 or SW2 passes S3 to SPK1 or SPK2, respectively.

Although not necessary according to the invention, the third signal S3 preferably includes two frequency components that differ in frequency by an amount equal to the desired brain wave frequency. For example, if the base frequency of the audio tone in the earphones is chosen to be 440 Hz (middle A) and the desired brain wave frequency is 10 Hz (in the Alpha range) the second frequency component of S3 would be chosen to be 440 Hz±10 Hz.

As is mentioned above, experimental results indicate that the human brain "cancels out" or "heterodynes" the frequencies and responds as if it were subject to the differential frequency. Since the frequency difference will in all cases be small (less than approximately 36 Hz, since the desired brain wave frequency will normally be in the Beta range or lower), both of these frequencies will normally fall easily within the pass-band of the third filter FLT3. It is not necessary to include two frequency components in the signal S3 if no "heterodyning" effect is sought. Rather, S3 may then be a simple single-frequency audio tone.

Figure 3:
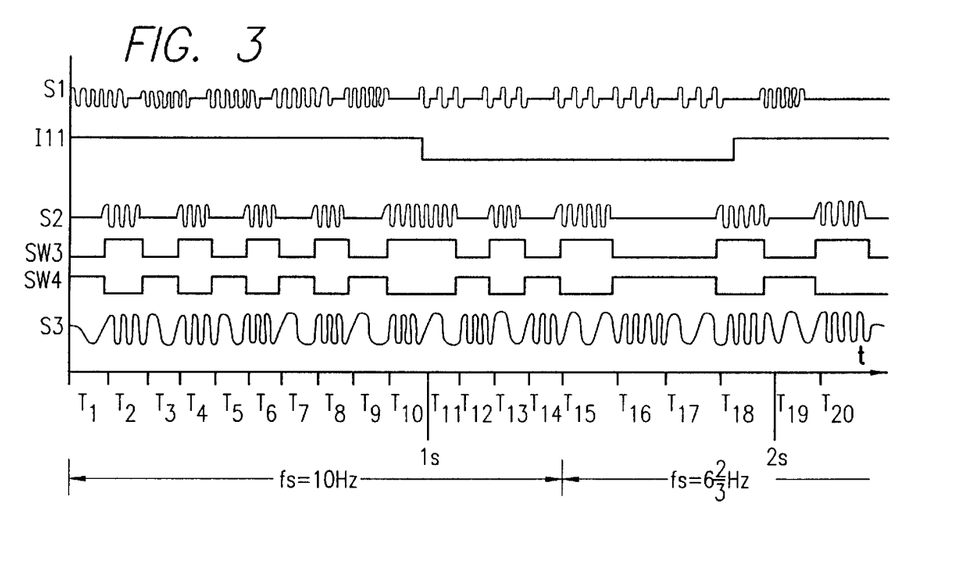
FIG. 3 illustrates graphically a simplified example of the structure and sequencing of a three-tone audio control track used as an input to the decoding and control circuitry.

FIG. 3 illustrates graphically an example of a portion of a time history of various signals in the circuit according to the invention. FIG. 3 does not show precise wave forms or amplitudes, but is rather a simplified, qualitative illustration of the timing and general relationship of the signals. According to the invention, signals S1, S2 and S3 are pre-recorded using known recording equipment onto a single track of the recording medium. Signal S3 is recorded directly. Signals S1 and S2 are processed prior to recording to make the number of sinusoids within each pulse proportional to the percent illumination desired. In FIG. 3, these signals are shown separately, that is, after separate filtering. On the control track of the recording medium, these three signals are superimposed on each other to form a single-track, multi-control signal.

One significant advantage of this invention is therefore that it is not necessary to provide special signal generators, timing circuitry, or specialized microprocessor programming in any component that the user would have to buy in order to use the invention; instead, all necessary control signals are generated in a recording studio, and can then be put easily on a large number of inexpensive standard cassette tapes. Furthermore, the number of different synchronization routines is not limited to some predetermined and preprogrammed set, but rather may be varied for all users simply by mass recording of a new routine onto cassette tapes that can be made available to all at low cost.

In FIG. 3, the left portion of the horizontal time axis is divided into fourteen 1/10th second intervals T1–T14. Since the period is equal to the inverse of the frequency, the synchronization frequency $f_s$ in these intervals is 10 Hz (in the Alpha range). This is chosen by way of example only. After the fourteen 1/10th second period, it is assumed, also by way of example, that the synchronization frequency $f_s$ is to drop to 6 2/3 Hz, corresponding to a signal period of 15/100 seconds. Six such period T15–T20 are illustrated in FIG. 3.

The second signal S2 controls the flashing of the second light LED2. Over the first ten periods T1–T10 S2 is present when S1 is absent. This means that the two lights LED1 and LED2 flash alternately. This is not necessary according to the invention. Rather, during the intervals T11, T13, and T15, S1 and S2 are synchronized, so that the lights will flash simultaneously. Since S1 and S2 are independent of each other, any pattern of flashing can be created simply by recording the two signals S1 and S2 with the desired sequencing.

The signal S3 determines the audio tone that the user will hear in the earphones or speakers SPK1 and SPK2. In the example shown in FIG. 3, the signal S3 alternates between two frequencies. This frequency shift is optional according to the invention, but if it is used, the frequency difference should preferably be equal to the desired synchronization frequency $f_s$. (In FIG. 3, the wave form for signal S3 is illustrated in greatly simplified form for the sake of clarity; for a base tone of 440 Hz, for example, signal S3 will go through 44 full cycles during each interval T1 through T10.) In the example shown in FIG. 3, the signal S3 has its higher frequency during each even-numbered time interval (T2, T4, T6, etc.) and its lower frequency during each odd-number interval. The signal S3 is recorded easily using known signal synthesizers and recording equipment.

During the first ten periods T1–T10 of the example illustrated in FIG. 3, the user will see lights that flash alternately left-right at a frequency of 10 Hz, and will hear a tone that switches back and forth between the left and right ears at a frequency of 10 Hz. Additionally, the tone heard in the one ear will be 10 Hz higher than the tone heard in the other ear.

According to the invention, the intensity of the flashing lights LED1 and LED2 can be controlled and varied according to a predetermined program during the original recording of the control track, for example, on a master tape.

During the time intervals T11–T15, the user will see lights that flash simultaneously in both eyes, with an intensity less than during the preceding ten intervals. The user will still, however, hear alternating tones of a slightly different frequency from ear to ear. During the time intervals T17–T20, the user will once again see alternating flashing lights at the lower intensity, and will hear alternating tones of slightly different frequency but during these intervals the synchronizing frequency will be lower since the "burst" and "pause" periods of the signals S1 and S2 are longer than during the first ten time intervals. Of course, in actual use a given frequency of lights and tones will normally continue for much longer than is illustrated in FIG. 3, but they do not necessarily have to do so; any pattern is possible by suitable pre-recording of the control signals S1, S2, and S3. As is mentioned above, the frequencies of the control signals S1, S2, and S3 should be separated sufficiently so that each filter FLT1, FLT2, and FLT3 will be able to reject that two control signals other than the control signal at or near its center frequency.

One advantage of the invention is that most of the components in the decoder/controller are readily available in the market and are inexpensive. Furthermore, components such as the active filters are readily available as small, inexpensive, integrated circuits incorporated into single chips. This helps to keep the decoder/controller both small and affordable. No signal generation circuitry is required, since the frequencies and timing of the control signals are arranged in advance during the recording of the control track of the cassette tape.

By centralizing the control function to the original recording studio that makes a master tape, no separate expensive microprocessor-controlled signal generation is required by the user.

Note that the playback speed of standard cassettes, compact discs, etc., is standardized, so that a control or audio signal recorded at, say, 5 Hz will not be "stretched" or "compressed" significantly during playback. Furthermore, the frequency of the "bursts" (typically at the synchronization frequency) will not change substantially if the tape speed is kept within the limits normally found in conventional tape players.

In an alternative embodiment, the present invention is adapted for use with a personal computer or similar device. For the sake of illustration, the following discussion applies the present invention to an IBM compatible computer, but it is clear that the present invention can be used on other computing devices.

In a preferred embodiment, the brain synchronization program and audio program are easily stored in the computer hard drive, floppy, CD-ROM disk, digital tape drive, or like data storage medium. With the user at the keyboard, the brain synchronization program and audio program are called up and executed in the RAM through processes well-known in the art.

Through conventional software commands, various pins in a parallel interface port of the PC are selectively activated. The activated pins in the parallel port in turn are used to actuate the LEDs in a spectacle configured as shown above. Further, selected pins are used to transmit an audible signal to earphones worn by the user. Although a parallel port is used, other interfaces are possible. For example, a game card port, a sound card port, or the like can be used for output of the brain synchronization program data and the audible program to the LEDs and earphones, respectively.

Figure 5:
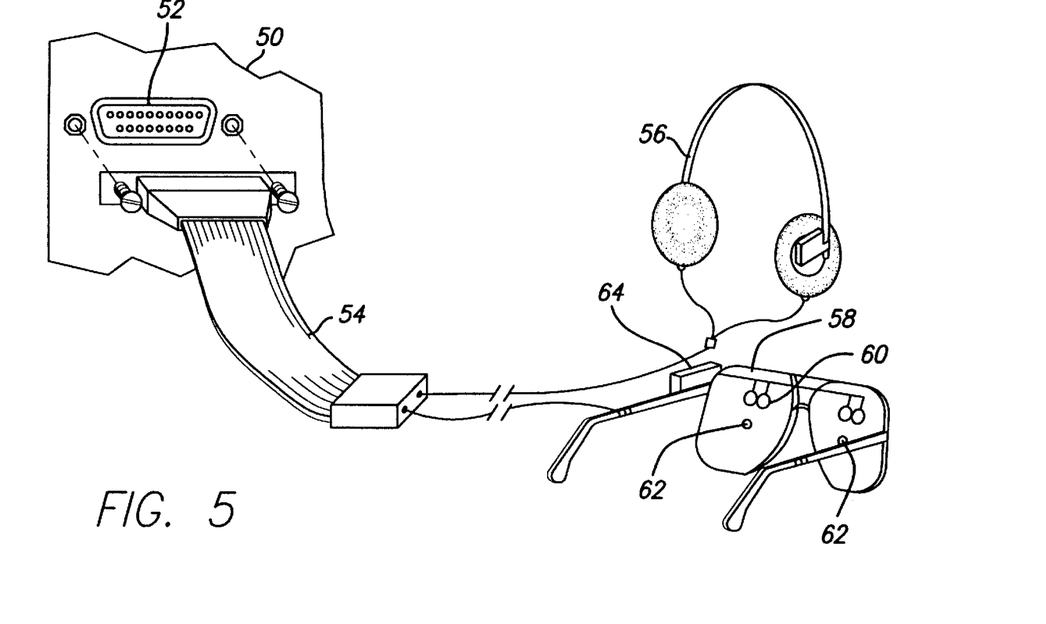
FIG. 5 shows an alternative embodiment of the present invention having a control source originating from a PC via a parallel port, and incorporating a motion sensor in the spectacles.

FIG. 5 shows the above alternative embodiment. The personal computer 50 is shown in a cutaway view, and can be of any configuration known in the art. In the back of the computer 50 is a standard Centronics or like parallel interface port 52, again known in the art. The parallel port 52 can receive or transmit data. TABLE 1 shows the industry standard configuration of the parallel port, as follows:

TABLE 1

| PIN | SIGNAL |
|---|---|
| 1 | −STROBE |
| 2 | DATA0 |
| 3 | DATA1 |
| 4 | DATA2 |
| 5 | DATA3 |
| 6 | DATA4 |
| 7 | DATA5 |
| 8 | DATA6 |
| 9 | DATA7 |
| 10 | −ACK |
| 11 | BUSY |
| 12 | PAPER EMPTY |
| 13 | +SELECT |
| 14 | AUTO FDXT |
| 15 | −ERROR |
| 16 | −INIT |
| 17 | −SLCTIN |
| 18–25 | GROUND |

In a typical computer, DATA pins 2 through 9 each is approximately +5 volts with a limit of 20 mA and are used by one embodiment of the instant invention; however, the present invention is not restricted to pins 2 through 9, nor is it restricted to the parallel port 52. Other user interface ports may be used insofar as data can be readily transferred into and out of the computer.

As mentioned above, very simple software containing the desired brain wave synchronization program and audible program can be written by any qualified computer programmer. The software is stored in a variety of media and executed by the microprocessor in the personal computer through any conventional process. The computer hardware is standard and does not form a part of the present invention; therefore, it is not shown in detail in FIG. 5.

The synchronization program and audible program in the present embodiment contain the same data as in the above embodiment. The data is sent through the DATA pins of the parallel port 52 to cable 54, and suitable divided and channeled to a headset 56 with earphones and to a pair of spectacles 58 configured as before. LEDs 60 mounted on the spectacles 58 are in turn operated by the synchronization program, while the audible program is reproduced in the headset 56. The 5-volt output voltage from the DATA pins are adequate to drive the transducers in the headset 56 as well as triggering the LEDs 60.

The spectacles 58 include optional peep holes 62 allowing the user to look through the spectacles 58 and see images on the computer monitor. This enables coordination between an audio stimulus and a visual stimulus which enhances the performance of the device. For example, when the present invention induces the user into an Alpha brain wave state in which the brain is conditioned for learning, a visual program containing a foreign language lesson can be viewed simultaneously on the monitor.

In yet another alternative embodiment, the present invention provides an optional Delta wave sensor, used to keep the user from falling asleep and transitioning into the Delta wave state. In an exemplary embodiment shown in FIG. 5, the Delta wave sensor is a common motion sensor 64 positioned on the spectacles 58 worn by the user. When operative, the Delta wave motion sensor 64 detects the attitude of the user's head. As the user enters the Theta wave state, she may become drowsy and her head inevitably drops with the chin down. The motion sensor 64 mounted on the spectacles 58 she is wearing then detects this change in attitude and triggers, preferably, a tone generator to produce an audible tone. The tone alerts and awakes the user, causes her to raise her chin in attention, and forces her back into the Theta state thus preventing her from passing into the Delta wave sleep state. In effect, the present invention becomes a bio-feedback device.

The motion sensor 64 and tone generator are devices well known in the art. In an exemplary embodiment, the motion sensor 64 can be a simple mercury tilt switch that, when inclined at a certain angle, closes a circuit to activate the tone generator. Preferably, the motion sensor 64 is set up on the spectacles 58 so that when the user's head tilts forward beyond a 45 degree angle, the tone generator is set off.

As a modified bio-feedback device, the present invention can incorporate a circuit known in the art that increases the frequency of the signal output from the tone generator when triggered by the motion sensor. Accordingly, the flashing of the LEDs increases in frequency to keep the user's brain synchronized in the Theta wave state, which user might otherwise have drifted off into the Delta state. Similarly, the motion sensor can trigger an increase in the frequency of the audible tone, again forcing the user back into the Theta wave state.

The motion sensor and tone generator including the power source and speaker can be entirely self-contained, as shown in FIG. 5, or the devices may be separated. For instance, in another alternative embodiment, the tilt switch is used to send a control signal through the parallel port to flag the executing program that the user is close to passing into the Delta wave state. In response, a subroutine in the program can cause an alarm tone to be generated and sent to the headset. This accomplishes the same purpose as the separate tone generator mounted in the spectacles.

Figure 6:
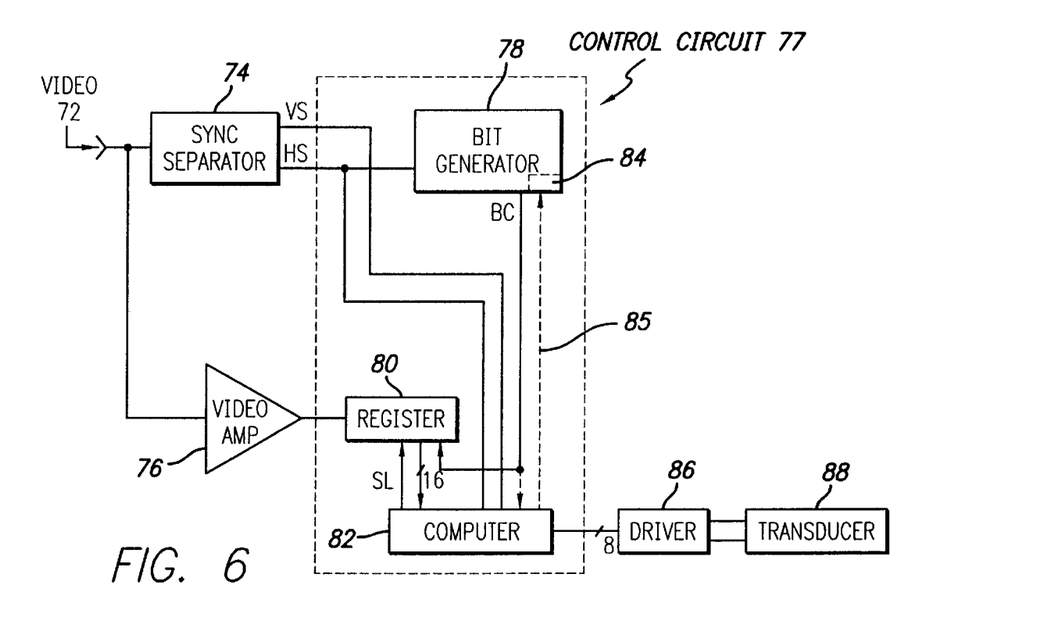
FIG. 6 shows a video decoder sensory stimulation system for stimulating the senses of a user based on encoded video data.

Having set forth the description above, substantially as contained in the parent application, further aspects of the present invention are now disclosed. Referring to FIG. 6, in one aspect of the present invention a video decoder sensory stimulation system 70 receives a composite video signal 72, including encoded sensory stimulation data, such as brain wave synchronization data, and converts or transforms the data into a control output for operating a sensory stimulation transducer. The principles inherent in this aspect may be adapted for use with virtually any video signal originating from virtually any source. The present invention also may implement a broad array of encoding schemes. Also, a variety of sensory stimulation transducers may be used, including, but not limited to, the foregoing brain wave synchronization transducers (light emitting diodes, visors, or audio speakers), odor producing transducers, vibrating transducers, or the like. Additionally, any such transducer can be controlled in a flexible manner to provide various forms of sensory stimulation, such as, for example, inducing brain waves in accord with the details of the foregoing disclosure.

The video decoder sensory stimulation system 70 includes a conventional video synchronization pulse extractor, or separator 74 receiving a composite video signal 72. The sync separator 74 extracts the horizontal and vertical synchronization pulses from the composite video signal 72. The vertical (VS) and horizontal (HS) synchronization pulses are respectively provided as first and second outputs. A conventional video amplifier 76 also receives composite video signal 72, providing an amplified or detection output signal to register 80.

A control circuit 77 includes a bit generator 78 which accepts the horizontal synchronization pulses as input from the sync separator 74 and provides a bit clock (BC) output to serial shift register 80. Computer, microprocessor, or digital processing device 82 also accepts the horizontal and vertical synchronization pulses as input from the sync separator 74. Computer 82 generates a select line signal (SL) in response to computations performed on the vertical and horizontal synchronization pulses, and outputs the select line signal to the serial shift register 80. Computer 82 includes at least one digital port comprising, for example, 8-bits.

The foregoing arrangement allows the serial shift register 80 to capture, or store, encoded sensory stimulation data contained in a horizontal line of the video signal 72. The data is transferred to computer 82 which operates on the encoded data, under program control, to convert or transform the data into control bits, or a control word, provided as output at a digital port. A digital to analog converter, or other driver 86 accepts the control word as input and provides an output which operatively drives a sensory stimulation transducer 88. The transducer may produce odors, flash lights, provide audio output, vibrate, or otherwise stimulate a user's senses. Overall, the video decoder sensory stimulation system 70 decodes sensory stimulation data encoded in virtually any video signal (from any source or medium) and flexibly controls the manner in which sensory stimulation is provided to a user of the system.

The construction and operation of video decoder sensory stimulation system 70 will now be discussed in greater detail. Various standards are used for producing video signals, such as National Television Systems Committee (NTSC), phase alternation each line (PAL), and sequential color with [avec] memory (SECAM). Due to its flexible implementation the present invention is adaptable for use with virtually any existing or future video scheme. In general, conventional video signals are designed to reproduce, on a video screen, a sequence of frames of visual scenes. Each frame may contain one field (progressive scanning) or more than one field (interlaced scanning). Each field is composed by sequentially tracing a number of horizontal lines across the video screen at a fast rate so that the viewer sees a complete image.

Vertical and horizontal synchronizing signals are used to coordinate the reproduction of a video image on the screen. A vertical synchronizing pulse causes the screen to begin the display of a new field. A sequence of horizontal synchronizing pulses cause a number of lines to be traced across the screen in rapid sequence to complete the display of the field. Another vertical synchronizing pulse then causes the screen to begin the display of the next field. In interlaced systems, one frame is composed of two or more field scans. In progressive systems, a frame is usually composed of only one field scan. Although the synchronizing signals control the scan pattern of the display, the video signal includes other signals governing the content of the image. The combination of signals is commonly referred to as the "composite video" signal.

The present invention utilizes encoded information embedded in one or more lines of the video signal to carry sensory stimulation data, such as brain wave synchronization data. It should be noted that not all lines of a video signal are necessarily displayed on a screen. Therefore, it is possible to embed sensory stimulation data in a video signal without significantly interfering with the display of an accompanying video image. For example, the sensory stimulation data can be included in undisplayed lines, the first few displayed lines, and/or the last few displayed lines. None of these embedding schemes would interfere with the display of a properly arranged video image.

Referring more particularly to FIG. 6, the composite video signal 72 is received by the video decoder sensory stimulation system 70. The video synchronization separator 74 extracts the vertical synchronization pulses and the horizontal synchronization pulses from the composite video signal 72. The sync separator 74 provides these pulses as independent first and second outputs. The sync separator 74 preferably comprises a conventional device such as Elantec model El 4583, or the equivalent. The purpose of separating the vertical and horizontal pulses is to allow the control circuit 77 to pinpoint the exact location of the embedded sensory stimulation data within the field.

The composite video signal is also received by the conventional video amplifier 76. This amplifier is preferably operated in a non-linear fashion so that the embedded sensory stimulation data can be recovered as a sequence, or serial train, of digital values. In other words, the output of the amplifier is preferably designed to assume one of two output levels based on the encoded value of the embedded sensory stimulation data. This can be accomplished using any number of schemes, including, but not limited to, the use of a saturated open loop amplifier, a schmidt trigger arrangement, or the like. The conventional video amplifier 76 may be comprised of conventional devices readily available from semiconductor vendors. It should be noted that the output of the amplifier is ignored when a non-encoded line is being scanned, as will become evident below. The purpose of the video amplifier is to recover or reproduce the encoded sensory stimulation data from the composite video signal.

A control circuit 77 receives the outputs from both the sync separator 74 and the video amplifier 76 and responsively controls the output of at least one sensory stimulation transducer 88, such as a brain wave synchronization transducer. The control circuit 77 comprises bit generator 78, serial shift register 80, and computer 82, which are operatively interconnected. The purpose of the control circuit is to capture, or temporarily store embedded sensory stimulation data and to convert or transform the data into an output for driving the sensory stimulation transducer 88 in a desired manner.

The bit generator 78 receives horizontal synchronization pulses which are output from the sync separator 74 and responsively produces or provides a bit clock signal to the shift register 80. The bit generator 78 preferably comprises a conventional phase locked loop for precisely detecting the phase of the incoming horizontal synchronization pulses and for providing a phase referenced square wave (or pulsed) output having a frequency which is a multiple of the horizontal synchronization pulse frequency. In other words, the bit generator 78 acts as a frequency multiplier and phase reference operating on the horizontal sync pulses. One device which may be configured to perform this function is the generic CMOS 4046 chip, or integrated circuit, available from vendors such as Motorola or National Semiconductor. The purpose of the bit generator 78 is to provide an appropriately timed shift clock so that the serial shift register 80 captures or temporarily stores the embedded sensory stimulation data at an appropriate rate.

A bit length value is provided to the bit generator 78 proportional to the number of data bits used to encode the embedded sensory stimulation data. The bit generator 78 may include a bit length counter 84 integral to its design which may be preloaded with the multiplication value or bit length value. An example of a suitable external counter device is ½ of a general CMOS 4520 chip, which may be loaded with a bit length value in a conventional fashion. Preferably, a bit length value is provided to the bit generator 78 directly from an output port of computer 82, under program control, eliminating the need for a separate, or external counter and adding design flexibility. This arrangement is indicated by the dashed bit length bus 85 in FIG. 6. Alternatively, program control could be used to preload an external counter. The purpose of providing a bit length value is to enable the control circuit 77 to adjust to the number of bits encoded in the embedded sensory stimulation data.

The computer 82 accepts the vertical synchronization pulses and horizontal synchronization pulses as input from the sync separator 74 and responsively enables the serial shift register 80 to store encoded sensory stimulation data when the display scan field reaches the line value of an encoded line. The computer 82 also converts or transforms the sensory stimulation data into a control word (a string of control bits) for operating a sensory stimulation transducer 88, such as a brain wave synchronization transducer. The computer can comprise almost any type of digital computer or microprocessor, or a more specialized micro-controller such as an Intel 8051, or related, device. The computer 82 preferably interfaces with serial shift register 80 over a one bit channel which may be termed the select line (SL).

Figure 7:
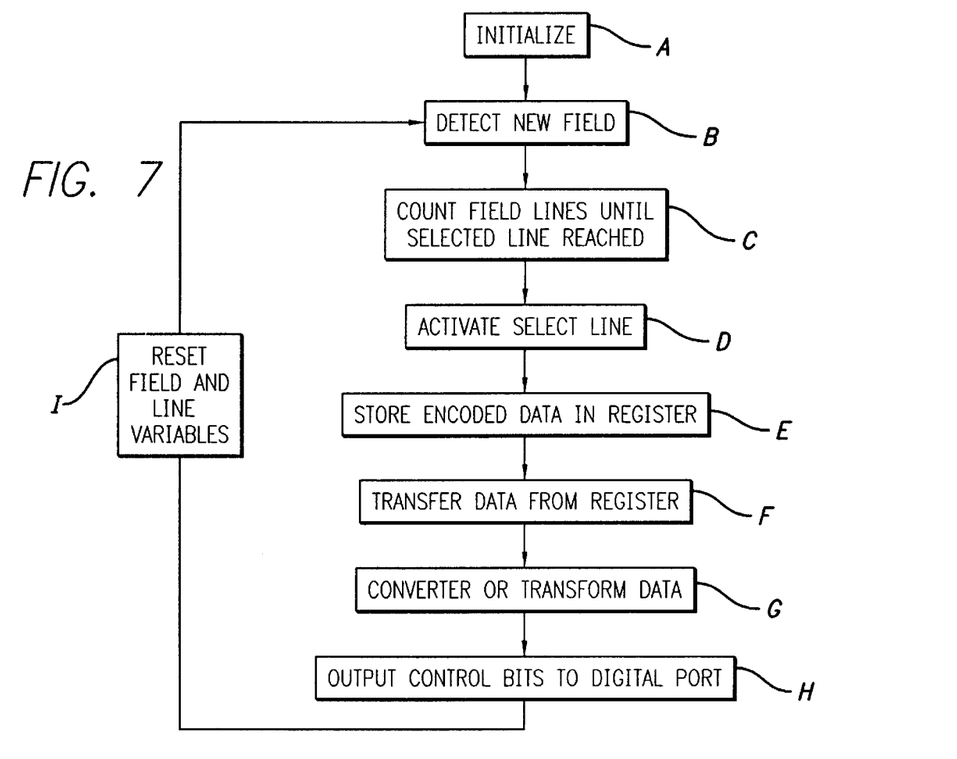
FIG. 7 shows a flow chart of the operation of a video decoder sensory stimulation system under program control.

Referring more particularly to FIG. 7 the computer 82 operates in conjunction with the register 80 by controlling the state of the select line and by controlling the transfer of data into the computer from the register. A program within the computer 82 is initialized during step A when the video decoder sensory stimulation system 70 is first turned on or otherwise activated to begin decoding. During this step, relevant counters are either set or reset and control parameter variables, such as the line select value, are assigned appropriate values.

In step B, the computer 82 monitors the vertical sync pulse input to detect a vertical sync pulse. This indicates the start of a new field in the composite video signal 72. Once a new field is detected, the computer 82 begins counting lines in the field in order to capture and store the encoded line at the appropriate moment, according to the following steps.

In step C, the computer 82 begins counting horizontal sync pulses as they occur on the horizontal sync pulse input to the computer. This is done by incrementing a counter, under program control, in the conventional fashion. By counting horizontal pulses, the computer is tracking the horizontal line currently being traced in the field of the video image.

When the horizontal sync count reaches the preset value assigned to, or corresponding to, the selected line, the computer 82 activates the select line (SL) signal in step D. This enables the serial shift register 80 to begin storing data. The selected line value is chosen so that it will correspond with the field line containing the encoded sensory stimulation data.

Activation of the select line (SL) enables the serial shift register 80 to begin storing sensory stimulation data sequentially in a conventional manner, which occurs during step E. While storage occurs, the select line (SL) remains activated and the bit generator 78 provides the bit clock (BC) to the serial shift register 80. The bit clock (BC) shifts data into register 80 one bit at a time, at a rate which is based on the horizontal sync pulse timing and the bit length value, as described above.

During step F, the computer 82 transfers the stored data from the register 80 over a parallel bus in the conventional manner. Conversion or transformation of the data into control bits or a control word occurs during step G. The conversion occurs under program control within the computer, and may be accomplished using a look-up table implemented in RAM, ROM, or other memory. In step H, the control bits are output to the driver 86 via an output port of the computer 82, effecting the control of sensory stimulation transducer 88. Step I provides for resetting loop variables such as a field flag and/or line counter, so that the program can repeat the above described process for subsequent video fields.

It should be noted that the operation of the video decoder sensory stimulation system 70 is described with respect to the particular steps above only for purposes of illustration and not of limitation. One of ordinary skill in the art would appreciate from the present disclosure that the steps need not necessarily be performed in the order or precise manner described. For example, loop variables may be reset at other points in the flow of operation.

Also, with reference to FIG. 6, the video decoder sensory stimulation system 70 may be configured in alternative manners other than the configuration specifically shown. For example, a 16 bit external register 80 is shown, corresponding to an encoded data bit length of 16 bits. This register may comprise any number of bits, however, to accommodate the number of bits of encoded data. An external register may be preferable when storage at a high rate is desired or when it is desired to provide a large number of encoded bits. However, the register 80 may alternatively be an integral component of the computer 82, such as the serial shift register available in an Intel 8051 family microcontroller. In such a case, the bit clock (BC) would then be input to the computer 82 instead of the register 80. Also, the functions of the bit generator could be integrated into the computer 82 in the form of a single integrated circuit. The operation described above is adaptable to this arrangement based on program implementation. Accordingly, the configuration shown in FIG. 6 should be construed as an example specifically illustrating the broad principles embodied in the present invention, and should not be construed as limiting the present invention to any particular circuit, embodiment, or particular choice of components.

Figure 8:
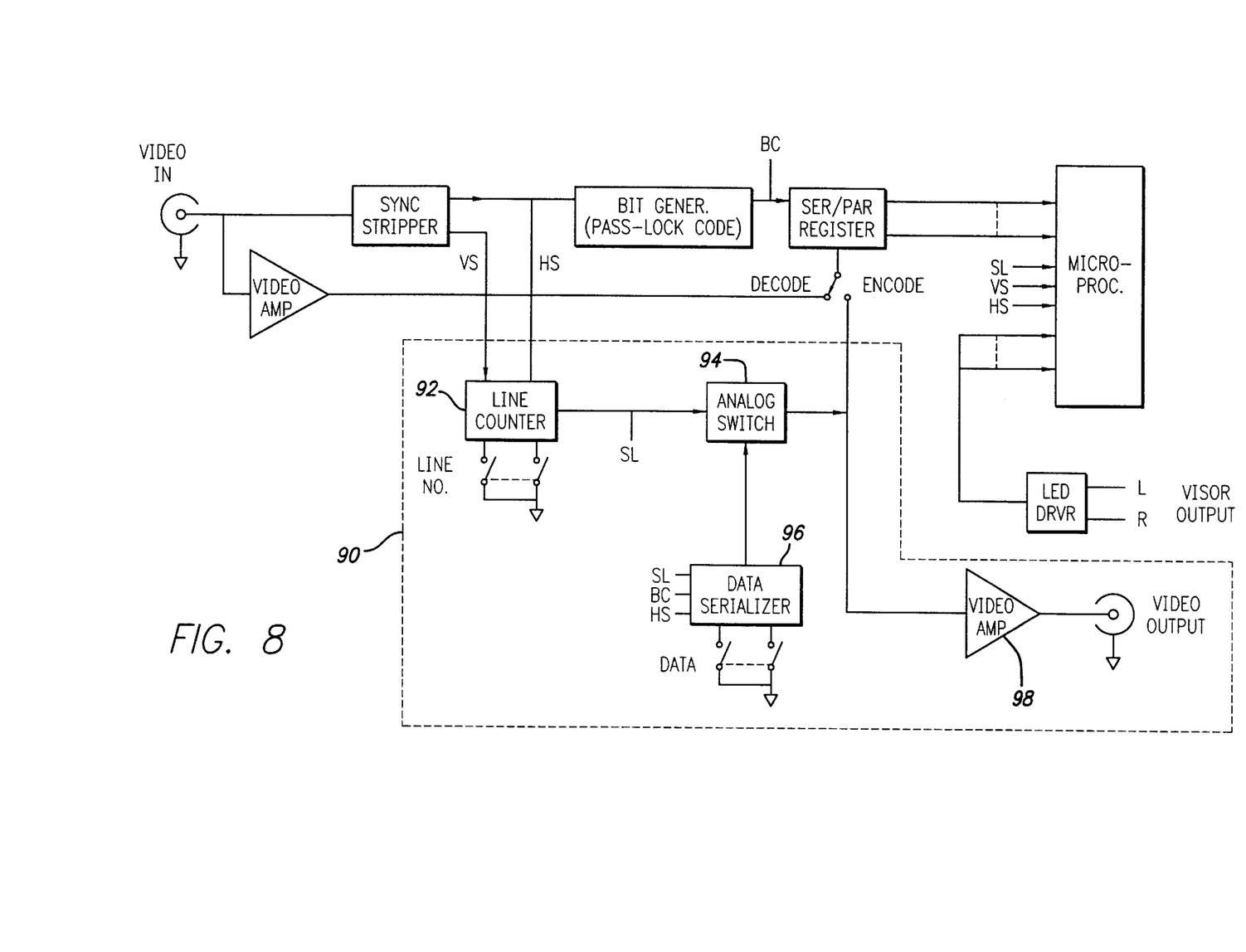
FIG. 8 shows an exemplary encoder circuit for embedding sensory stimulation data into an incoming video signal.

Referring to FIG. 8, an exemplary encoding circuit 90 is shown in dashed lines, suitable for implementing one form of encoding scheme for the present invention. The encoding circuit 90 is used in conjunction with a video decoder sensory stimulation system 70 in order to embed encoded data into an incoming video signal. The incoming video signal is designated "video in". Encoding circuit 90 receives the "video in" signal and, when the encode/decode switch is positioned in the encode position, embeds encoded sensory stimulation data into the appropriate line of the signal, providing the resulting signal as "video out". The encoded "video out" signal may be stored on tape or other suitable medium, or it may be simultaneously broadcast to remote decoders.

The video decoder sensory stimulation system 70, as shown in FIG. 8, is included substantially as described above. However, the video decoder sensory stimulation system 70 need not be included, as a whole, along with encoding circuit 90 in all encoding configurations.

Referring particularly to the operation of encoder circuit 90, line counter 92 turns on analog switch 94 when the line to be encoded in the "video in" signal is reached. The data serializer, or bit serial source 96 is set manually or automatically to provide encoded data to the video amplifier 98 through the analog switch 94 when the switch is turned on. In this manner, encoded data is embedded in the appropriate line of the "video out" signal. The embedded encoded data in the "video out" signal is recoverable by a video decoder sensory stimulation system 70 as described above. The line counter 92, analog switch 94, data serializer 96 and video amplifier 98 are all conventional elements available from vendors of electronic devices.

Figure 9:
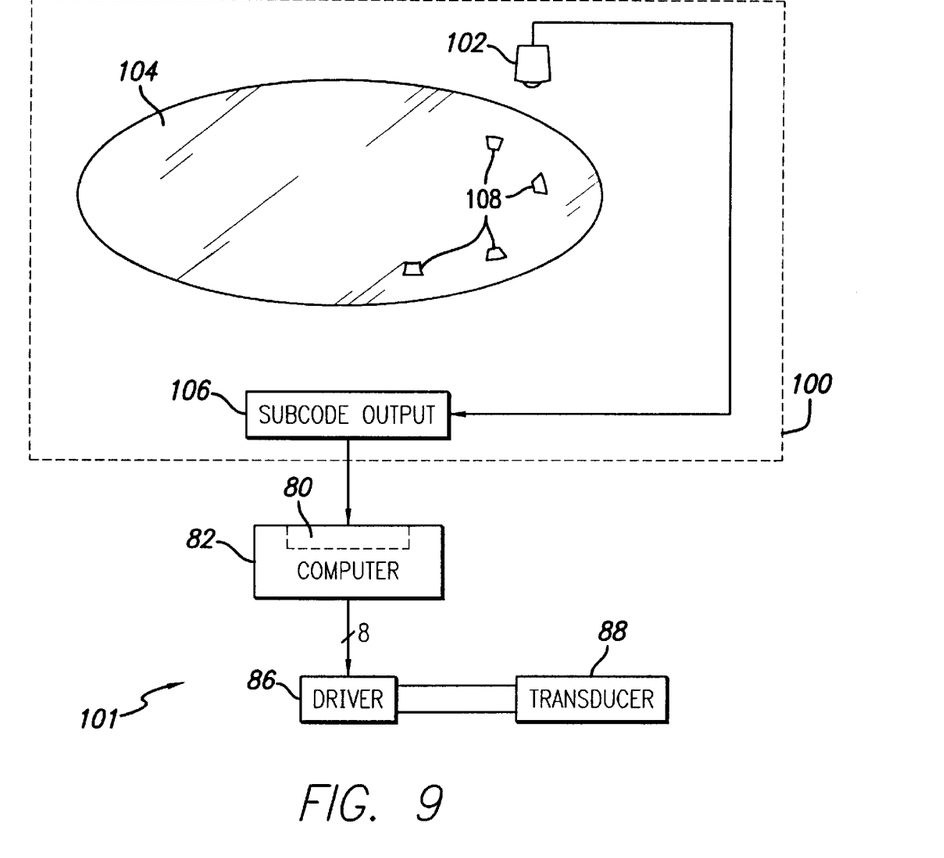
FIG. 9 shows a compact disk decoder sensory stimulation controller using a subcode region to store encoded sensory stimulation data.

Referring now to FIG. 9, in another aspect the present invention provides for digital decoding of sensory stimulation data from a compact disk, or similar, medium. The sensory stimulation data may comprise, for example, brain wave synchronization data for driving a brain wave synchronization transducer 88. Other types of sensory stimulation transducers may be used, however, such as buzzers, odor producing devices, or the like.

Referring more particularly to FIG. 9, a compact disk sensory stimulation controller 101 is shown. Compact disk (CD) player 100 includes conventional apparatus for accessing data in subcode regions, indicated by exemplary subcode regions 108. The details of subcode standards, which apply to professional CD equipment, are provided in the American National Standards Institute publication ANSI S4.40-1992, or in the Audio Engineering Society publication A.E.S. 3-1992. A subcode standard which applies to consumer CD devices is published by the International Electronics Commission as I.E.C. 958. In general, compact disks and disk players are designed to include and access subcode regions 108 in addition to other data regions, usually according to one of the above standards.

FIG. 9 illustrates symbolically a subcode reader 102 connected to a subcode output block 106. The subcode output 106 is typically available directly from an output jack included with a conventional CD player 100. The present invention uses data embedded in the subcode regions of a compact disk surface to operate a sensory stimulation transducer 88 through a controller or computer 82.

In this aspect, encoded sensory stimulation data is serially transferred to register 80 at a rate consistent with any of the protocols detailed in the subcode standards. Alternatively, parallel transfer may be possible with appropriate modifications. The register 80 may be an internal register, integral with the computer 82, or it may be an external register, as previously described. Computer 82 operatively monitors the contents of register 80 and responsively transforms or converts the encoded data into control bits, or a control word, as described above for the video decoder sensory stimulation system 70.

Using this arrangement transducers 88, such as brain wave synchronization transducers (previously described), may be operated via the subcode functions of the CD player without resorting to the use of resources devoted to the usual audio/DAC (digital to analog conversion) functions of the CD player. This would allow for brain wave synchronization control via suitable transducer 88 to proceed along with any conventional audio, visual, or audio-visual output from the CD player.

In yet another aspect of the present invention, brain wave entrainment during brain wave synchronization is enhanced in the user of a light producing device, wherein the device operatively delivers light to the user's retina or retinas. Ordinarily, the user of such a device achieves a certain degree of brain wave synchronization commonly referred to as the brain wave "entrainment" of the user. The entrainment of a user has been considered by some experimenters to be a function of the apparent light intensity observed by the user. However, the present inventor has observed some correlation evidencing an enhancement of the user's entrainment by increasing the actual peak intensity of delivered light for a given apparent intensity.

Accordingly, brain wave entrainment may be enhanced by pulsing the light producing device in a manner which produces the same apparent light intensity in the user while increasing substantially the actual light intensity delivered to the user's retina. The present method may be used with various light producing devices, including, but not limited to, light emitting diodes, strobe lights, flash devices, bulbs, or the like. An exemplary apparatus for implementing the present method is shown in FIG. 11.

Figure 10A:
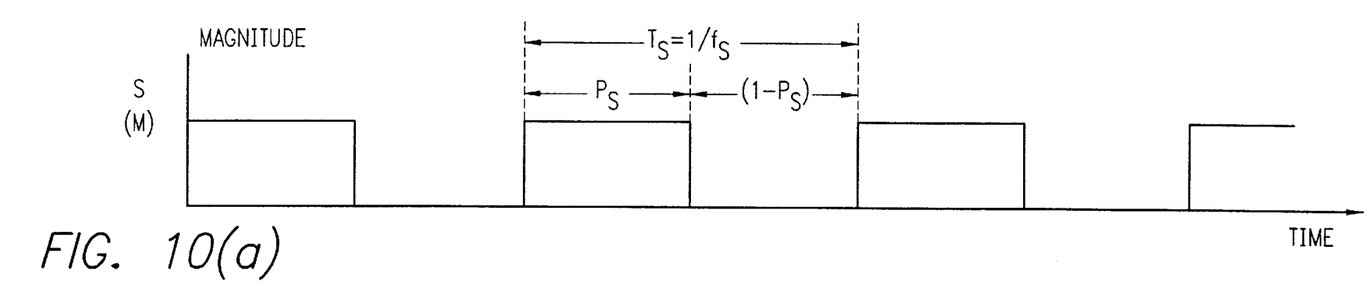
FIGS. 10a, 10b and 10c show composite and component waveforms illustrating the principles for pulsing a light producing device to enhance brain wave entrainment according to the present invention.
Figure 10B:
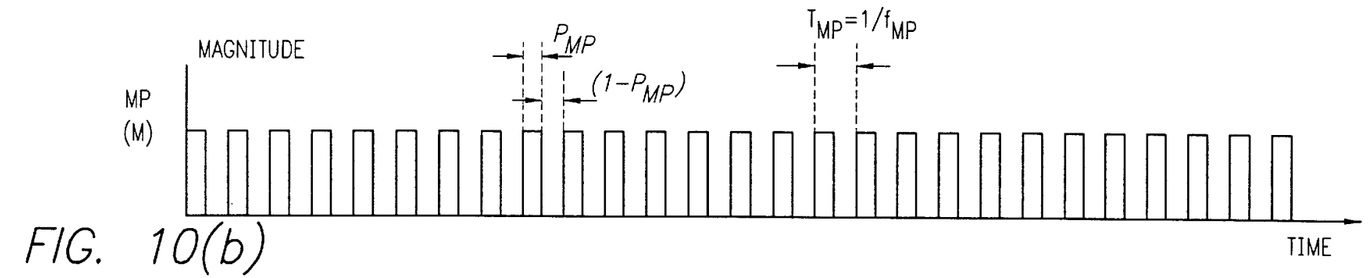
Figure 10C:
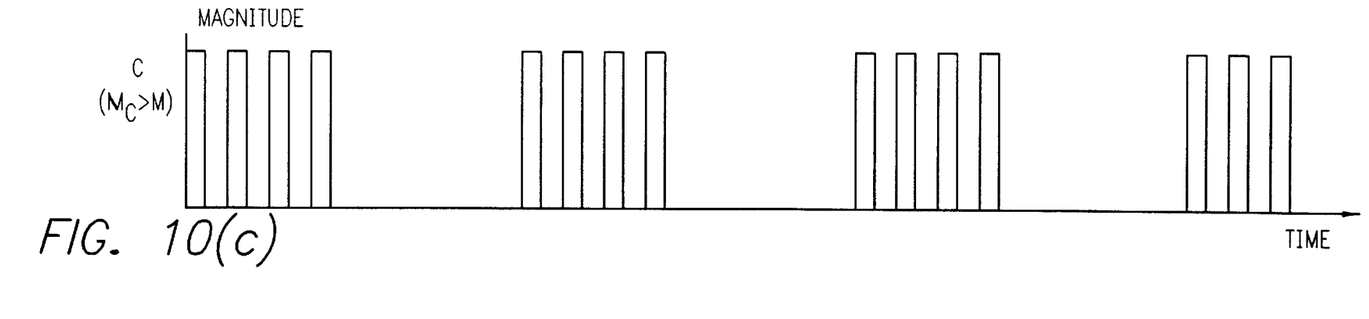
Figure 11:
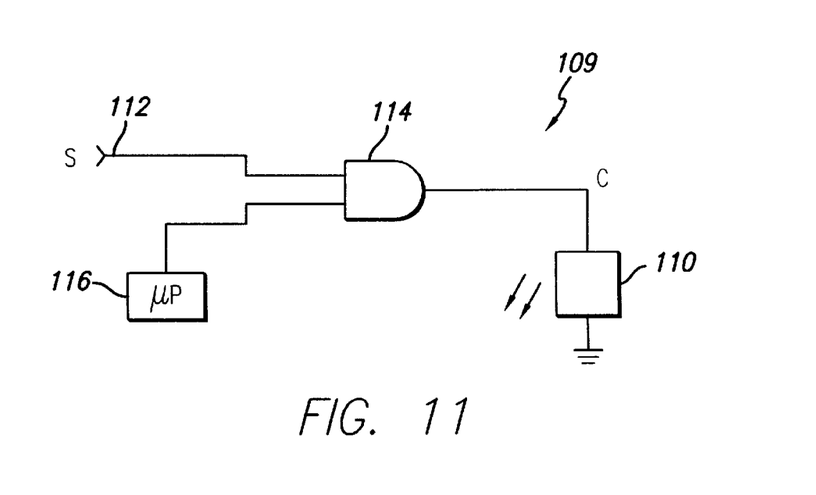
FIG. 11 shows an exemplary pulse driver circuit for pulsing a light producing device in accord with the principles of the present light pulsing method.

Referring to FIG. 11 a pulse driver 109 is shown which may either comprise, or be incorporated into, driver 86 (shown in FIGS. 6 and 9). Pulse driver 109 receives a synchronization frequency signal, or component, "S" from computer 82, or any other suitable source, such as a conventional subcircuit of driver 86. A typical timing diagram of signal "S" is shown in FIG. 10(a). A micro-pulse signal, or component, "MP" is provided by oscillator 116, which may be a conventional oscillator. A typical timing diagram of signal "IMP" is shown in FIG. 10(b). A combining circuit or driving device 114 receives each of the component signals "S" and "MP" and responsively provides as output a composite signal "C" for driving the light producing device 110. An exemplary timing diagram of composite signal "C" is shown in FIG. 10(c).

FIGS. 10(a)–10(c) illustrate that the composite signal "C" is synthesized, or derived from the synchronizing component "S" and the micro-pulse component "MP". For the example shown, the composite signal "C" is provided by implementing the logical AND function of the component signals "S" and "MP", and by increasing the magnitude of "C" with respect to "S" and "MP". This can be accomplished, for example, by using a power AND gate as the combining circuit or driving device 114 of FIG. 11. If the light producing device 110 is chosen to be a light emitting diode, the power AND gate provides a suitably pulsed, increased magnitude composite current signal "C" for driving the LED. Oscillator 116 may be provided using a standard 556 integrated circuit timer configured in a conventional manner.

Preferably, the frequency of the synchronizing component "S" ($f_s$) is in the 1 hz–30 hz range, or in any range suitable for inducing brain wave synchronization in the user of the light producing device, as disclosed above. The period of the synchronizing component ($T_s$) is inversely proportional to its frequency. The duty cycle of the synchronizing component ($P_s$) may be any value, usually less than one, and preferably it will be 0.5 (50%). However, it is contemplated that other duty cycle values would be equally appropriate.

Preferably, the frequency of the micro-pulse component "MP" ($f_{mp}$) is 2800 hz, or in any range substantially exceeding the synchronization component frequency ($f_s$). The period of the micro-pulse component ($T_{mp}$) is inversely proportional to its frequency. The duty cycle of the micro-pulse component ($P_{mp}$) may be any value, usually less than one, and preferably it will be 0.5 (50%). However, it is contemplated that other duty cycle values would be equally appropriate.

Preferably, there is no correlation between the parameters of the two component signals, "S" and "MP". However, it is possible to derive parameters for the "MP" signal from the "S" signal, such as, for example, providing the micro-pulse component "MP" as a harmonic frequency of the synchronization component "S". One way to accomplish this would be to provide the "S" signal as input to a conventional phase-locked loop which would responsively provide the "MP" signal as a harmonic multiple thereof. The "S" and "MP" components could then be combined in any suitable manner, such as using the AND gate 114.

Alternatively, the duty cycles of the two signals may be related or correlated using conventional pulse width modification techniques and circuits. Also, it may be desirable in some cases to derive the magnitude of the composite signal ($M_c$) from some combination of parameters of the component signals, including magnitude, frequency, and/or duty cycle. For example, it may be advantageous to provide a relationship wherein the magnitude of the composite signal $M_c$ increases linearly as the duty cycle of one or both component signals is reduced. Non-linear relationships may also be implemented consistent with the teachings and principles embodied in the present method and apparatus.

One of ordinary skill in the art would recognize that the magnitude of the composite signal "C" is governed by the output characteristics of driving device 114 and the load characteristics of light producing device 110.

Additionally, it is noted that various light producing devices provide light intensities which vary in proportion to a driving signal based on the particular device characteristics. It is contemplated that individual light producing devices would be adjustable accordingly based on the teachings disclosed above.

Although the foregoing disclosure relates to specific embodiments, the principles of the present invention inherent in such embodiments should be recognized and broadly construed, as one of ordinary skill in the art would understand. Accordingly, the invention should not be limited to the details of any particular disclosed embodiment, but should be broadly interpreted with respect to the following claims.

What is claimed is:

1. A sensory stimulation device for presenting simultaneously to a user both a video image derived from a video signal and non-video sensory stimulus according to sensory stimulation data encoded within said video signal, the device comprising:

a detection circuit for receiving said video signal and extracting said non-video sensory stimulation data encoded therein;

a video output port for providing output to a video screen in accordance with said video signal;

at least one sensory stimulation transducer; and a control circuit operating on said extracted encoded data for responsively controlling said at least one sensory stimulation transducer.

2. A device as claimed in claim 1, wherein said detection circuit comprises:

a pulse separator receiving said video signal and responsively providing first and second synchronizing pulse outputs; and an amplifier receiving said video signal and responsively providing a detection output; said control circuit comprises a bit generator receiving at least one of said first and second synchronizing pulse outputs and responsively providing a clock indication;

a computer receiving said first and second synchronizing pulses and responsively generating a select indication; and a register receiving said detection output, said clock indication, and said select indication, and responsively storing said encoded data as a plurality of bits;

said computer operating on said plurality of stored bits and responsively providing control bits at a digital port;

and wherein said sensory stimulation transducer is operatively connected to said digital port.

3. A device as claimed in claim 2, wherein:

said first and second synchronizing pulses are vertical and horizontal synchronizing pulses, respectively; and said pulse separator comprises a video synchronization separator extracting said vertical and horizontal synchronizing pulses from said video signal.

4. A device as claimed in claim 3, wherein said bit generator comprises a phase-locked loop and further receives a bit length value, providing said clock indication responsively to said bit length value.

5. A device as claimed in claim 4, wherein said video signal includes at least one frame corresponding to said vertical synchronization signal;

said frame includes a plurality of lines corresponding to said horizontal synchronization signal;

said computer includes a selected line value stored in memory for indicating a line containing said encoded data;

said register comprises a shift register;

said bit length value corresponds to the number of bits in said register;

said clock indication further comprises a number of periods proportional to said bit length value;

said computer counts said vertical and horizontal synchronization pulses and responsively provides said select indication to said register;

wherein said register stores said encoded data from said selected line in response to said clock indication and said select indication.

6. A device as claimed in claim 5, wherein said sensory stimulation transducer comprises a light emitting device and wherein said encoding data is transformed into a brain wave synchronization signal for inducing brain wave synchronization.

7. A device as claimed in claim 2, wherein said bit generator comprises a phase-locked loop.

8. A device as claimed in claim 2, wherein said register comprises a shift register.

9. A device as claimed in claim 2, wherein said computer further includes memory;

said memory storing a look up table for transforming said plurality of stored bits into said control bits;

wherein said encoded data is transformed to a corresponding stimulation signal output from said sensory stimulation transducer for stimulating the senses of a user.

10. A device as claimed in claim 2, wherein said register is integrally part of said computer.

11. A device as claimed in claim 2, wherein said register is externally provided from said computer.

12. A device as claimed in claim 1, wherein said sensory stimulation transducer comprises a light emitting device.

13. A device as claimed in claim 1, wherein said sensory stimulation transducer comprises an audio emission device.

14. A device as claimed in claim 1, wherein said sensory stimulation transducer comprises an odor emitting device.

15. A device as claimed in claim 1, wherein said sensory stimulation transducer comprises a light emitting device and wherein said encoding data is transformed into a brain wave synchronization signal for inducing brain wave synchronization.

16. A brain wave synchronization device comprising:

a storage medium comprising a compact disk surface having at least one allocated subcode region including encoded sensory stimulation data;

a retrieval device comprising a subcode reader portion of a compact disk player for accessing data from said storage medium and serially providing an encoded output;

a control circuit including:
a register receiving said encoded output and storing it as a plurality of bits;
a processor, including a digital port, operatively monitoring the value of said plurality of bits in said register and responsively transforming said plurality of stored bits into a plurality of control bits provided to said digital port; and
at least one sensory stimulation transducer operatively connected to said digital port.

17. A device as claimed in claim 16, wherein said sensory stimulation transducer comprises a light emitting device.

18. A device as claimed in claim 17, wherein said sensory stimulation transducer comprises an audio emission device.

19. A device as claimed in claim 16, wherein said computer further includes memory;

said memory storing a look up table for transforming said plurality of stored bits into said control bits;

wherein said encoded data is transformed to a corresponding stimulation signal output from said sensory stimulation transducer for stimulating the senses of a user.

20. A device as claimed in claim 16, wherein said sensory stimulation transducer comprises an odor emitting device.

21. A device as claimed in claim 19, wherein said sensory stimulation transducer comprises a light emitting device and wherein said encoded data is transformed into a brain wave synchronization signal for inducing brain wave synchronization.

22. A device as claimed in claim 16, wherein said sensory stimulation transducer comprises a light emitting device and wherein said encoding data is transformed into a brain wave synchronization signal for inducing brain wave synchronization.

23. A device as claimed in claim 16, wherein said register is integrally part of said computer.

24. A device as claimed in claim 16, wherein said register is externally provided from said computer.

25. A method of producing brain wave synchronization in a user of a light producing device, the device operatively delivering light having an apparent intensity and an actual peak intensity to the user's retina, comprising:

pulsing the light producing device with a composite signal derived from a synchronization frequency component and a micro-pulse component, said synchronization frequency and micro-pulse components having respective duty cycles, frequencies, and magnitudes, said micro-pulse component frequency being greater than 40 Hz, wherein said pulsing provides a higher peak intensity for a given intensity, thereby enhancing the brain wave entrainment of the user.

26. The method as claimed in claim 25, wherein the frequency of the micro-pulse component is approximately 2800 Hz.

27. The method as claimed in claim 26, wherein the magnitude of the composite signal is substantially increased above a magnitude limit for the synchronization frequency component used alone.

28. The method as claimed in claim 26, wherein the duty cycle of the micro-pulse component is variable.

29. The method as claimed in claim 26, wherein the duty cycle of the synchronization component is variable.

30. The method as claimed in claim 26, wherein the frequency of the micro-pulse component is proportional to the frequency of the synchronization component.

31. The method as claimed in claim 26, wherein the duty cycle of the micro-pulse component is proportional to the duty cycle of the synchronization component.

32. The method as claimed in claim 26, wherein the magnitude of the composite signal is proportional to at least one of the parameters of said micro-pulse component, said parameters including a duty cycle, a frequency, and a magnitude.

33. The method as claimed in claim 26, wherein the magnitude of the composite signal is proportional to at least one of the parameters of said synchronization component, said parameters including a duty cycle, a frequency, and a magnitude.

34. A device producing brain wave synchronization in a user, comprising:
   a light producing element operatively delivering light to the retina of the user having an apparent intensity and an actual peak intensity;
   said light being delivered in pulses having frequency greater than the approximate threshold of human visual perception, such that the pulses have a peak intensity exceeding the apparent intensity observed by the user; wherein brain wave entrainment of the user is enhanced by the use of higher peak intensity light.

35. The device of claim 34, wherein the light producing element comprises a light emitting diode.

36. The device of claim 34, wherein said light producing element is driven by a composite signal including a synchronization component and a micro-pulse component.

37. The device of claim 36, further including a driving device providing said composite signal as output to said light producing element.

38. The device of claim 37, wherein said driving device receives as input said synchronization component and said micro-pulse component and responsively provides said composite signal output.

39. The device of claim 38, wherein said driving device comprises a logical AND gate.

40. The device of claim 39, further including an oscillator circuit providing said micro-pulse component to said AND gate.

41. The device of claim 39, further including a wave form generator receiving said synchronization component and responsively providing said micro-pulse component.

42. The device of claim 41, wherein said wave form generator comprises a phase-locked loop.

43. A device as in claim 34 wherein:
   said pulse frequency is approximately 2800 Hz.

* * * * *